US006723851B2

(12) United States Patent
Miller et al.

(10) Patent No.: US 6,723,851 B2
(45) Date of Patent: Apr. 20, 2004

(54) CHEMILUMINESCENT COMPOUNDS AND USE THEREOF

(75) Inventors: Phillip Miller, Dana Point, CA (US); Martha Garrity, San Clemente, CA (US)

(73) Assignee: Quest Diagnostics Investment Incorporated, Wilmington, DE (US)

( * ) Notice: Subject to any disclaimer, the term of this patent is extended or adjusted under 35 U.S.C. 154(b) by 32 days.

(21) Appl. No.: 09/999,700

(22) Filed: Oct. 31, 2001

(65) Prior Publication Data

US 2003/0092060 A1 May 15, 2003

(51) Int. Cl.$^7$ .......................... C07L 17/02; C07L 17/14; C07D 219/06; G01N 33/533; G01N 33/535; G01N 33/553
(52) U.S. Cl. .................. 546/104; 435/7.5; 435/7.95; 546/102
(58) Field of Search ................... 546/102, 104

(56) References Cited

U.S. PATENT DOCUMENTS

| | | |
|---|---|---|
| 4,150,134 A | 4/1979 | Schulenberg |
| 4,745,181 A | 5/1988 | Law et al. |
| 4,918,192 A | 4/1990 | Law et al. |
| 4,927,769 A | 5/1990 | Chang et al. |
| 4,946,958 A | 8/1990 | Campbell et al. |
| 4,950,613 A | 8/1990 | Arnold, Jr. et al. |
| 5,108,893 A | 4/1992 | Baret |
| 5,110,932 A | 5/1992 | Law et al. |
| 5,185,439 A | 2/1993 | Arnold, Jr. et al. |
| 5,227,489 A | 7/1993 | Law et al. |
| 5,241,070 A | 8/1993 | Law et al. |
| 5,281,712 A | 1/1994 | McCapra et al. |
| 5,284,951 A | 2/1994 | McCapra et al. |
| 5,290,936 A | 3/1994 | Beheshti et al. |
| 5,321,136 A | 6/1994 | McCapra |
| 5,338,847 A | 8/1994 | McCapra |
| 5,395,752 A | 3/1995 | Law et al. |
| 5,395,938 A | 3/1995 | Ramakrishnan |
| 5,438,139 A | 8/1995 | Sato et al. |
| 5,445,936 A | 8/1995 | Piran et al. |
| 5,449,556 A | 9/1995 | Law et al. |
| 5,468,646 A | 11/1995 | Mattingly et al. |
| 5,468,649 A | 11/1995 | Shah et al. |
| 5,491,072 A * | 2/1996 | Akhavan-Tafti et al. |
| 5,521,103 A | 5/1996 | Zomer et al. |
| 5,538,901 A | 7/1996 | Law et al. |
| 5,543,524 A | 8/1996 | Mattingly et al. |
| 5,565,570 A | 10/1996 | Mattingly et al. |
| 5,594,112 A | 1/1997 | Sato et al. |
| 5,595,875 A | 1/1997 | Law et al. |
| 5,639,604 A | 6/1997 | Arnold, Jr. et al. |
| 5,656,207 A | 8/1997 | Woodhead et al. |
| 5,656,426 A | 8/1997 | Law et al. |
| 5,656,500 A | 8/1997 | Law et al. |
| 5,663,074 A | 9/1997 | Law |
| 5,665,328 A | 9/1997 | Horan et al. |
| 5,672,475 A | 9/1997 | Lee et al. |
| 5,681,695 A | 10/1997 | Decker et al. |
| 5,702,887 A | 12/1997 | Law et al. |
| 5,705,330 A | 1/1998 | Shah et al. |
| 5,705,338 A | 1/1998 | Piran et al. |
| 5,756,011 A | 5/1998 | Woodhead et al. |
| 5,783,453 A | 7/1998 | Barlow et al. |
| 5,783,696 A | 7/1998 | Kinkel et al. |
| 5,783,699 A | 7/1998 | Mattingly et al. |
| 5,858,668 A | 1/1999 | Neuenhofer et al. |

FOREIGN PATENT DOCUMENTS

WO      01/09372 A1 *   9/2001

* cited by examiner

*Primary Examiner*—Mary E Ceperley
(74) *Attorney, Agent, or Firm*—Stout, Uxa, Buyan & Mullins, LLP; Donald E. Stout; Greg S. Hollrigel

(57) ABSTRACT

A novel chemiluminescent compound is provided. In one embodiment, the novel compound is employed in an assay to detect analytes. The assay to detect analytes includes the steps of binding the novel compound to the analyte and detecting the novel compound.

1 Claim, No Drawings

CHEMILUMINESCENT COMPOUNDS AND USE THEREOF

SUMMARY OF THE INVENTION

This invention relates to a group of novel compounds. In one embodiment, the novel compounds are novel chemiluminescent compounds.

Furthermore, it has been discovered that these compounds offer tremendous benefits when they are employed as "signal molecules" in chemical or biochemical assays. "Signal molecules" are molecules which are detected to determine the level of analytes in the sample. It has been surprisingly discovered that the assays employing these compounds have sensitivities that are several orders of magnitudes over that of other chemiluminescent assays, for example the presently existing assays employing acridinium esters. For example, the limit of detection (LOD) for the present immunoassays with acridinium esters is in the range of $10^{-15}$ to $10^{-18}$ moles of analyte, whereas the LOD for assays employing the novel compound is in the range of about $10^{-16}$ to $10^{-19}$, preferably $10^{-17}$ to $10^{-20}$ moles of analyte.

Additionally, the methods for detecting analytes of the present invention are safe and simple. For example, the present assays do not require the use of radioactive isomers. Also, the novel compounds employed in these methods are highly compatible with blood and other clinical specimens.

In accordance with the present invention, the method of detecting an analyte comprises the steps of binding compound to the analyte and/or the immediate surrounding areas, and detecting the amount of the bound compound.

Further in accordance with the present invention, the binding of the compound to the analyte and/or the immediate surrounding area may be catalyzed by an enzyme.

Still further in accordance with the present invention, the bound compounds emit chemiluminescent signals and the signal are detected. In one embodiment, the amount of chemiluminescent signals emitted is directly proportional to the amount of analyte in the sample.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DETAILED DESCRIPTION OF THE INVENTION

The present invention is, in part, based upon the discovery that a novel compound may be employed in an assay to detect analytes.

The novel compound (Compound A) has the general formula A:

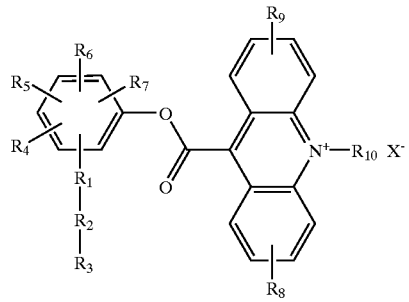

wherein R1 and R2 are independently selected from the group consisting of a bond, C1–C10 hydrocarbon, substituted alkyl, unsubstituted alkyl, aryl, peptide, $(CH_2)_mSO_2$, $NH(CH_2)_m$, $(CH_2)_m$,

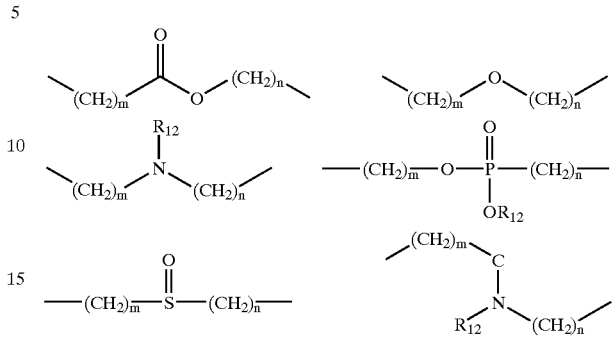

R1 may be located anywhere on the ring. For example, R1 may be at the ortho, meta or para position. R3 is OH or

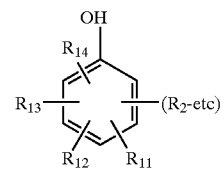

R4, R5, R6, R7, R8, R9, R10, R11, R12, R13 and R14 may be located anywhere on the ring and are independently selected from the group consisting of a H, hydroxide, methyl, $(CH_2)_mSO_3$, halide, nitro, —CN, —SO3, C1–C10 hydrocarbon, alkoxy, —NHC=O(C1–C10 hydrocarbon), —C=O(C1–C10 hydrocarbon), C=ONH(C1–10 hydrocarbon), aryl, and cyclic ring structure; m and n are independently 0 to about 10; X is a counter ion including $CH_3SO_4^-$, $OSO_2F^-$, $Cl^-$ $Br^-$, $OSO_2CH_3^-$ and $OSO_2C_4H_9^-$.

In one embodiment, R1 is $(CH_2)_mSO_2$ and R2 is NH $(CH_2)_m$. For example, the novel compound (Compound B) may have the general formula B:

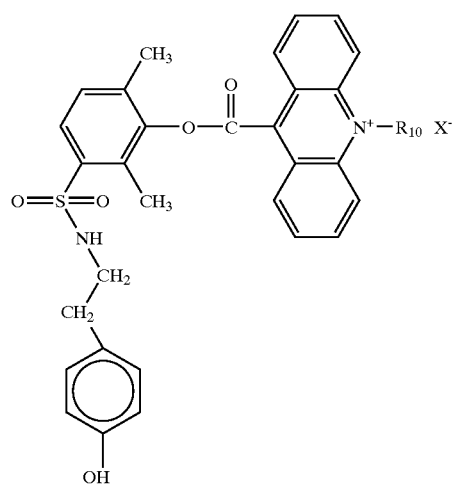

$R_{10}$ may be a methyl or a $(CH_2)_3SO_3$.

In one embodiment, the novel compound has a shelf life in excess of six months, preferably in excess of a year. For example, a compound of this invention may be stored at pH of about 5 to about 7, and at a temperature of about 2 to about 8 degrees Celsius for over a year.

In one embodiment, a compound of this invention may include a deposition component and an acridinium derivative. Deposition components are components which may be activated, for example by enzymes, and deposit at a local area. Non-limiting deposition components include penicillins, cephamycins, substituted phosphates, beta-glactopyranosylglycoside and the like. Non-limiting examples of acridinium derivatives, preferably acridinium ester derivatives, which may be employed within this invention, are disclosed in the following U.S. Pat. Nos., all of which are incorporated by referenced herein in their entireties: Schulenberg, U.S. Pat. No. 4,150,134; Law et al., U.S. Pat. No. 4,745,181, and U.S. Pat. No. 4,918,192; Chang et al., U.S. Pat. No. 4,927,769; Campbell, U.S. Pat. No. 4,946,958; Arnold, Jr. et al., U.S. Pat. No. 4,950,613; Law et al., U.S. Pat. No. 5,110,932; Arnold, Jr. et al., U.S. Pat. No. 5,185,439; Law et al., U.S. Pat. No. 5,227,489; Law et al., U.S. Pat. No. 5,241,070; McCapra et al., U.S. Pat. No. 5,281,712; McCapra et al., U.S. Pat. No. 5,284,951; Beheshiti et al., U.S. Pat. No. 5,190,936; McCapra et all, U.S. Pat. No. 5,321,136 and U.S. Pat. No. 5,338,847; Law et al., U.S. Pat. No. 5,395,752; Ramakrishnan, U.S. Pat. No. 5,395,938; Sato et al., U.S. Pat. No. 5,438,139; Law et al., U.S. Pat. No. 5,449,556; Mattingly et al., U.S. Pat. No. 5,468,646; Shah et al., U.S. Pat. No. 5,468,649; Zoomer et al., U.S. Pat. No. 5,521,103; Law et al., U.S. Pat. No. 5,538,901; Mattingly et al., U.S. Pat. No. 5,543,524 and U.S. Pat. No. 5,565,570; Sato et al., U.S. Pat. No. 5,594,112; Law, U.S. Pat. No. 5,595,875; Law et al., U.S. Pat. No. 5,656,426; Law, U.S. Pat. No. 5,656,500; Law, U.S. Pat. No. 5,663,074; Lee et al., U.S. Pat. No. 5,672,475; Law et al., U.S. Pat. No. 5,702,887; Kinkel et al., U.S. Pat. No. 5,783,696; and Mattingly et al., U.S. Pat. No. 5,783,699. In one embodiment, the deposition component and the acridinium derivative directly link to each other. In another embodiment, the deposition component and the acridinium component is linked through another molecule, a linker. The linker may be molecules that are similar to that of R1.

The novel compound of this invention may be employed in an assay to detect an analyte. An analyte may be any chemical or biological substance. Non-limiting examples of analytes include hormones, peptides, macromolecules, macromolecules, proteins, tissues, mixtures thereof and the like. The compound of the present invention may be adaptable for use in various types of assays, for example, gel, blotting, in situ hybridization, and immunohistochemical assays.

In a broad embodiment, the method of detecting an analyte in a sample includes binding the compound to the analyte. In one embodiment, the compound may bind to areas immediately surrounding the analyte.

Without wishing to limit the invention to any theory or mechanism, it is believed that a compound of the present invention could bind to an analyte and other molecules, proteins and areas immediately surrounding the analyte when the compound is exposed to an enzyme, for example a peroxidase, preferably a horseradish peroxidase (HRP).

In one embodiment, the enzyme is brought close to the analyte to initiate the binding of the compound to the analyte and/or the surrounding molecules and areas. For example, a locator component may be employed to locate the analyte.

A locator component is any molecule or set of molecules capable of selectively binding to an analyte. For example, a locator component may be an aptamer or a molecular imprint polymer. In one embodiment, a locator component is an antibody, or a portion of an antibody, for example a Fab portion, capable of binding to an analyte. The antibody of the present invention may be monoclonal or polyclonal. Various methods are known in the art to produce an antibody specific toward a certain antigen, for example a partner component. For example, an antibody may be raised from a rabbit injected with an antigen, the antigen being the partner component or a part thereof. Additionally, synthetic antibodies may also be made. (See U.S. Pat. No. 5,110,833, the disclosure of which is incorporated in its entirety by reference herein.)

In one embodiment, the locator component is directly or indirectly attached to an enzyme. Non-limiting examples of enzymes include peroxidase, horseradish peroxidase, oxireductase, b-lactamase, hydrolase, lyase, transferase, isomerase, ligase, oxidase, phosphatase, esterase, glycosidase, and b-galactosidase. The selection of an appropriate enzyme is readily determinable by one of ordinary skill in the art. In one embodiment, a beta-lactamase is used in an assay employing a deposition component comprising a penicillin or a cephanycin. In one embodiment, a B-galactosidase is used in an assay employing a deposition component comprising a B-glactopyranosylglycoside.

In one embodiment, the assay sample comprising the analyte is first incubated with the locator component, for example an antibody, attached to (or tagged with) one or more enzymes, for example horseradish peroxidase. After the locator components attach to the analytes, compounds of the present invention are added to the sample. The enzymes attached to the locator component would cause the compounds of the present invention to bind to the analyte and/or matters and areas surrounding the analyte, including the locator component. Preferably, the binding of the compound of the present invention to the analyte is performed under basic conditions. For example, the assay is performed at a pH of about 7 to about 8.5.

After the compounds of the invention binds to the analyte and/or the areas immediately surrounding the analyte, the amount of compounds bound is measured.

In one embodiment, the amount of compounds bound is directly proportional to the amount of analyte in the sample.

In one embodiment, the compounds of the present invention emit chemiluminescent signals. Thus, amount of chemiluminescent emission detected from a sample directly relates to how much analyte there is in a sample. In one embodiment, the limit of detection for immunoassays with a compound of this invention is in the range of about $10^{-15}$ to about $10^{-18}$, preferably about $10^{-16}$ to $10^{-19}$, more preferably $10^{-17}$ to $10^{-20}$ moles of analyte. Furthermore, the dynamic range is very broad for the compounds of this invention, that is the emission of chemiluminescent signal by compounds of this invention may be linear for over 4 to about 6 orders of magnitude.

In one embodiment, the analytes may be immobilized for binding and/or detection. For example, a support having antibodies, which recognize the analytes, may be employed to immobilize the analytes to the support. Suitable supports used in assays include synthetic polymer supports, such as polystyrene, polypropylene, substituted polystyrene (e.g. aminated or carboxylated polystyrene), polyacrylamides, polyamides, polyvinylchloride, glass beads, agarose, nitrocellulose, nylon, polyvinylidenedifluoride, surface-modified nylon and the like.

The analytes may also be immobilized through the use of a biotinylated-antibody/strepavidin-coated-magnet particle system. Here, after the locator component binds to the analyte, the biotinylated-antibody binds the locator component. The strepavidin-coated-magnet particle may then complex with the locator component through the biotinylated-antibody. Other similar systems are disclosed in Garrity et al. U.S. patent application Ser. No. 09/761,969, the disclosure of which is incorporated in its entirety herein by reference.

EXAMPLE 1

Synthesis of Compound B

The synthesis was accomplished by adding an acridinium sulfonyl chloride derivative (2 mg, 36 μmole) to a solution of tyramine (6 mg, 44 μmole) in DMF (100 uL) and triethyl amine (50 uL). The product was isolated by preparative HPLC:$C_{18}$ [60/40 acetonitrile, $H_2O$(0.1% TFA)]. Compound B had a measurable light emission at 360 nm and a $t_r$ of 18 m.

EXAMPLE 2

Application of the Compound in an Assay

A 100 uL sample containing an analyte is added to a mixture of 50 uL botinylated antibody, 50 uL of HRP tag antibody, and 20 uL of streptavidin coated magnetic particles. The biotiylated antibody selectively binds the HRP tag antibody; the HRP tag antibody selectively binds the analyte; and the strepavidin coated magnetic particles selectively binds the biotinylated antibody. The resulting mixture is incubated at 37 degrees C. for 20 minutes after which the solid phase is separated magnetically and washed three times.

The washed solid phase is added to a second mixture. The second mixture includes (1) about 20 ul of a solution comprising about 0.2 to about 10 ug/mL of Compound A, preferably Compound B, in a 6.0 pH aqueous buffer and (2) about 200 uL of a solution comprising about 0.001 to about 0.1% hydrogen peroxide in a borate buffer at 7.0 to 8.4 pH. The second mixture is then incubated for about 1 to about 10 minutes at 37 degrees C. The solid phase of the second mixture is separated magnetically and washed three times.

The concentration of the compound is preferably measured by detecting the level of chemiluminescent emissions caused by the compound. The clemission of the compound is directly proportional to the concentration of the analyte. The chemiluminescence of the second mixture solid phase is triggered by the addition of about 200 uL of a solution of about 0.4 M nitric acid and about 0.1% hydrogen peroxide followed by about 200 uL solution of 1 M sodium hydroxide. The signal is accumulated over 2 seconds.

While this invention has been described with respect to various specific examples and embodiments, it is to be understood that the invention is not limited thereto and that it can be variously practiced with the scope of the following claims.

What is claimed is:

1. A compound of the formula:

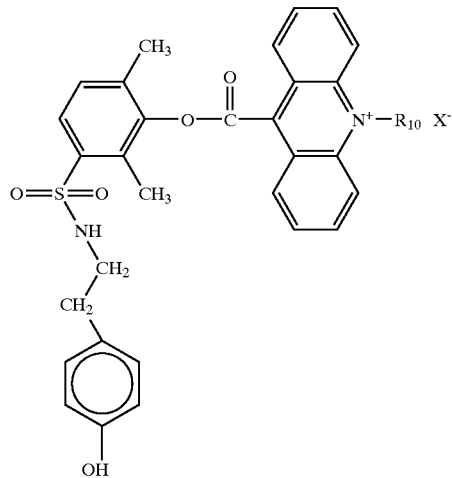

wherein $R_{10}$ is methyl or $(CH_2)_3SO_3$.

* * * * *